United States Patent
Inoue

(10) Patent No.: US 9,592,070 B2
(45) Date of Patent: Mar. 14, 2017

(54) METHOD FOR TREATING GASTROESOPHAGEAL REFLUX DISEASE

(71) Applicant: OLYMPUS CORPORATION, Hachioji-shi, Tokyo (JP)

(72) Inventor: Haruhiro Inoue, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 82 days.

(21) Appl. No.: 14/318,190

(22) Filed: Jun. 27, 2014

(65) Prior Publication Data
US 2015/0374352 A1 Dec. 31, 2015

(51) Int. Cl.
| A61B 17/32 | (2006.01) |
| A61F 5/00  | (2006.01) |
| A61B 17/00 | (2006.01) |

(52) U.S. Cl.
CPC ...... *A61B 17/320016* (2013.01); *A61B 17/00* (2013.01); *A61B 17/00234* (2013.01); *A61F 5/0083* (2013.01); *A61B 2017/00269* (2013.01); *A61B 2017/00827* (2013.01)

(58) Field of Classification Search
CPC A61B 2017/00818; A61B 2017/00827; A61B 2017/00269; A61B 17/00; A61B 17/00234; A61B 17/320016; A61F 5/0083
See application file for complete search history.

(56) References Cited

U.S. PATENT DOCUMENTS

| 2010/0168512 A1* | 7/2010 | Rahmani ......... A61B 17/12013 600/104 |
| 2010/0217288 A1* | 8/2010 | Baker ............... A61B 17/0401 606/151 |

OTHER PUBLICATIONS

H. Satodate et al., "Squamous Reepithelialization after Circumferential Endoscopic Mucosal Resection of Superficial Carcinoma Arising in Barrett's Esophagus," Endoscopy 2004, vol. 36, pp. 909-912.
H. Satodate et al., "Circumferential EMR of carcinoma arising in Barrett's esophagus: case report," *Gastrointestinal Endoscopy*, vol. 58, No. 2, 2003, pp. 288-292.
Journal of Japanese Society of Gastroenterology vol. 107, No. 4, 2010, pp. 549-558 (with partial translation).
*Medicina*, vol. 50, No. 5, 2013, pp. 867-872 (with partial translation).
Gastroenterology, vol. 52, No. 4, 2011, pp. 388-395 (with partial translation).
Journal of Japanese Society of Gastroenthrology, vol. 107, Annex A 138 (with partial translation) (2010).

* cited by examiner

*Primary Examiner* — Howie Matthews
(74) *Attorney, Agent, or Firm* — Oliff PLC

(57) ABSTRACT

There is provided a method of treating gastroesophageal reflux disease, which includes dissecting one of a mucosal layer and a submucosal layer of at least one of an esophagogastric junction and a stomach in a range less than an entire circumference of a circumferential direction so that moderate stenosis occurs due to cicatrization in an area in which one of the mucosal layer and the submucosal layer is dissected.

10 Claims, 4 Drawing Sheets

METHOD FOR TREATING GASTROESOPHAGEAL REFLUX DISEASE

BACKGROUND OF THE INVENTION

Field of the Invention

The present invention relates to a method of treating gastroesophageal reflux disease.

Description of Related Art

Gastroesophageal reflux disease is caused when contents of the stomach, mainly gastric acid, move backward into the esophagus causing unpleasant subjective symptoms such as heart burn or hyperacidity, and is an inflammatory disease of the esophagus causing pathological conditions such as esophagitis, Barrett's esophagus, or esophageal adenocarcinoma resulting from Barrett's esophagus.

Reflux of the gastric acid into the esophagus often occurs when the cardia is relaxed or an abdominal pressure increases. When there is a sliding esophageal hiatal hernia, since clamping of the cardia by the diaphragm is insufficient, reflux of the gastric acid into the esophagus is likely to occur.

SUMMARY OF THE INVENTION

According to an aspect of the present invention, a method of treating gastroesophageal reflux disease, the method includes dissecting one of a mucosal layer and a submucosal layer of at least one of an esophagogastric junction and a stomach in a range less than an entire circumference of a circumferential direction so that moderate stenosis occurs due to cicatrization in an area in which one of the mucosal layer and the submucosal layer is dissected.

One of the mucosal layer and the submucosal layer may be dissected in a range of ¼ or more of an entire circumference of the esophagogastric junction and less than the entire circumference thereof, the moderate stenosis may be induced in the esophagogastric junction, and an opening that is closed by contraction of a lower esophageal sphincter may be formed in the esophagogastric junction.

One of the mucosal layer and the submucosal layer may be dissected in at least a lesser curvature side of the stomach.

One of the mucosal layer and the submucosal layer may be dissected across a squamocolumnar junction in an area 30 mm toward a mouth from the squamocolumnar junction and in an area 30 mm toward an anus from the squamocolumnar junction out of the esophagogastric junction.

One of the mucosal layer and the submucosal layer may be dissected in an area of 30 mm or more and 50 mm or less from the mouth side to the anus side out of the esophagogastric junction.

When a distance from the mouth side to the anus side is measured in the area in which one of the mucosal layer and the submucosal layer is dissected in the esophagogastric junction, an area of the mouth side relative to the squamocolumnar junction may be wider than an area of the anus side relative to the squamocolumnar junction.

When the esophagogastric junction is located in a thoracic cavity side relative to a diaphragm due to a sliding esophageal hiatal hernia, one of the mucosal layer and the submucosal layer in the stomach may be dissected in a range less than an entire circumference of the stomach in a part of the stomach in contact with the esophageal hiatus so that the moderate stenosis may be induced in the stomach.

When the esophagogastric junction is located in a thoracic cavity side relative to a diaphragm due to a sliding esophageal hiatal hernia, the moderate stenosis may be induced in the esophagogastric junction.

One of the mucosal layer and the submucosal layer including at least a lesser curvature side of the stomach in at least one of the esophagogastric junction and the stomach may be dissected so as to form the moderate stenosis.

DETAILED DESCRIPTION OF THE INVENTION

According to preferred embodiments of the present invention, a narrowed opening at which gastric acid reflux may be prevented from passing from a stomach into an esophagus is formed, thereby preventing gastric acid from reaching the esophagus. Specifically, by forming incomplete cicatricial stenosis in either or both of the esophagus and the stomach, an opening capable of reducing dysphagia occurring when food passes and preventing gastric acid from refluxing is formed, thereby preventing the gastric acid from reaching the esophagus.

(Embodiment 1)

Figure 1:
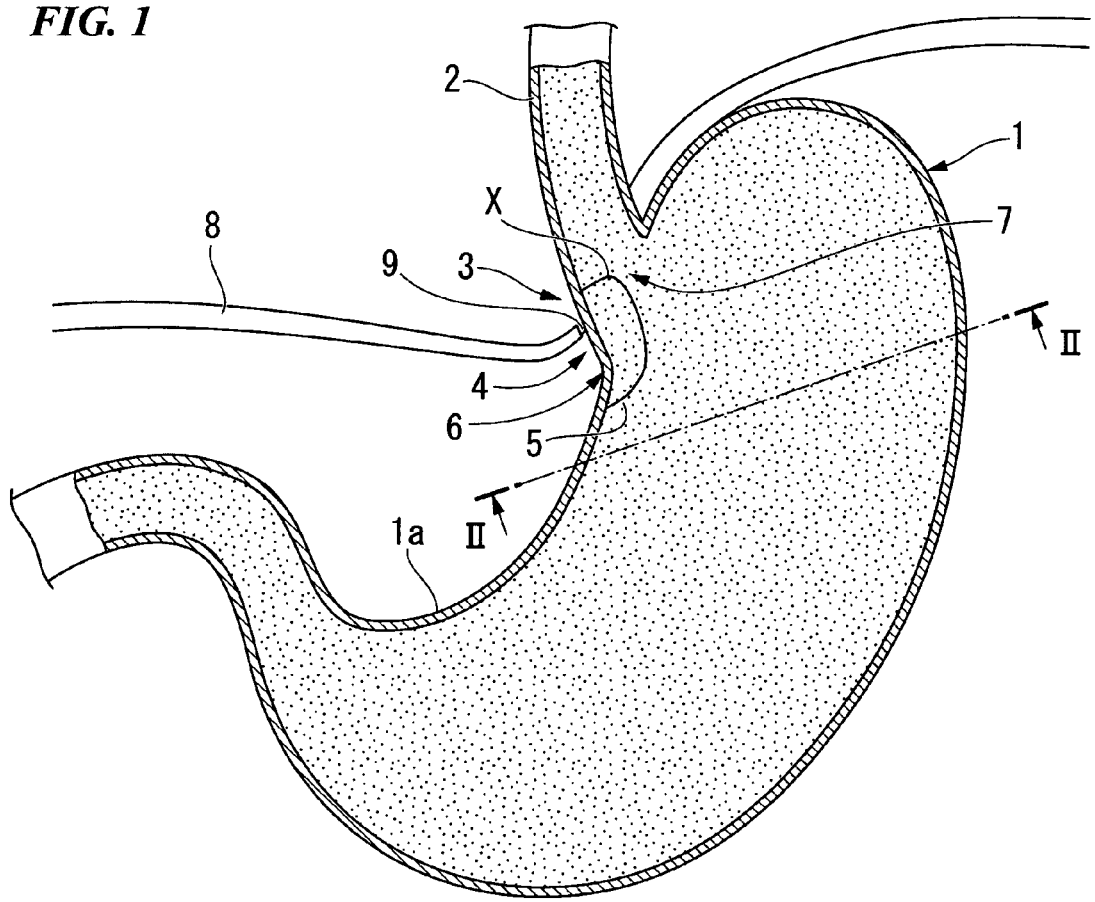
FIG. 1 is a diagram schematically showing a dissection area of a mucosal layer or a submucosal layer in Embodiment 1 of the present invention.
Figure 2:
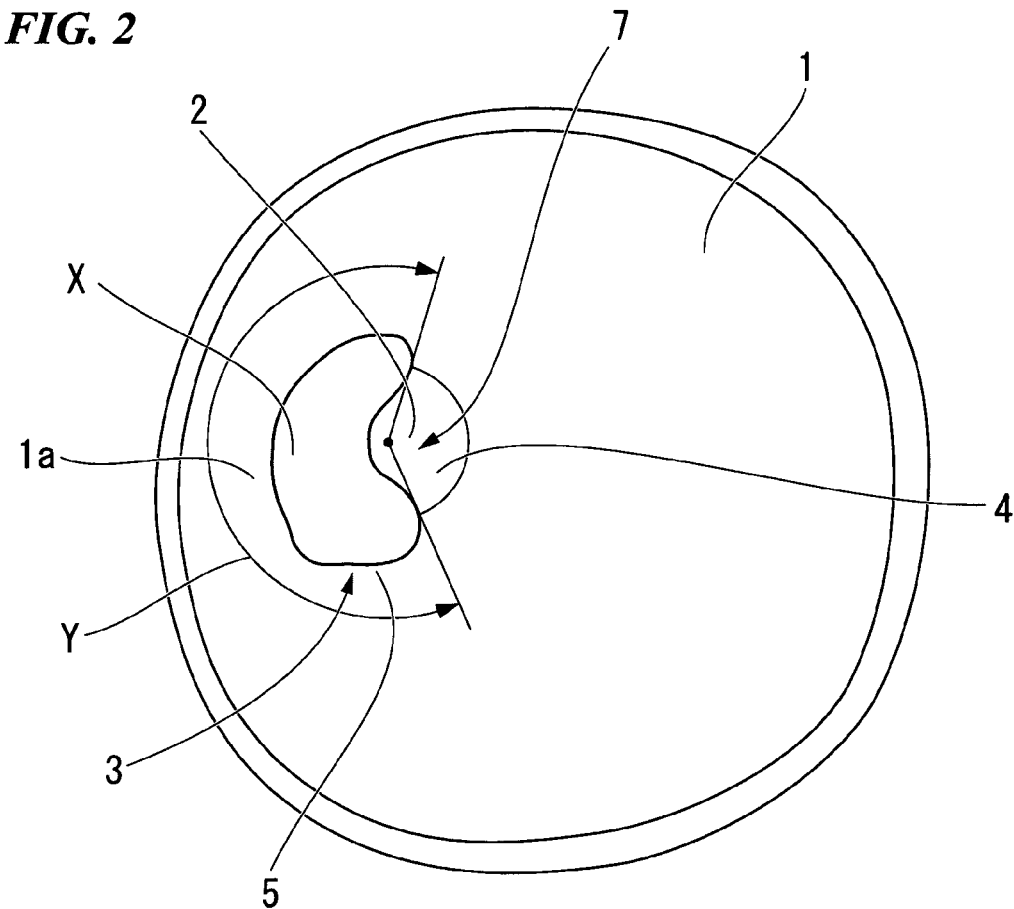
FIG. 2 is a diagram schematically showing a dissection area of a mucosal layer or a submucosal layer in Embodiment 1.
Figure 3:
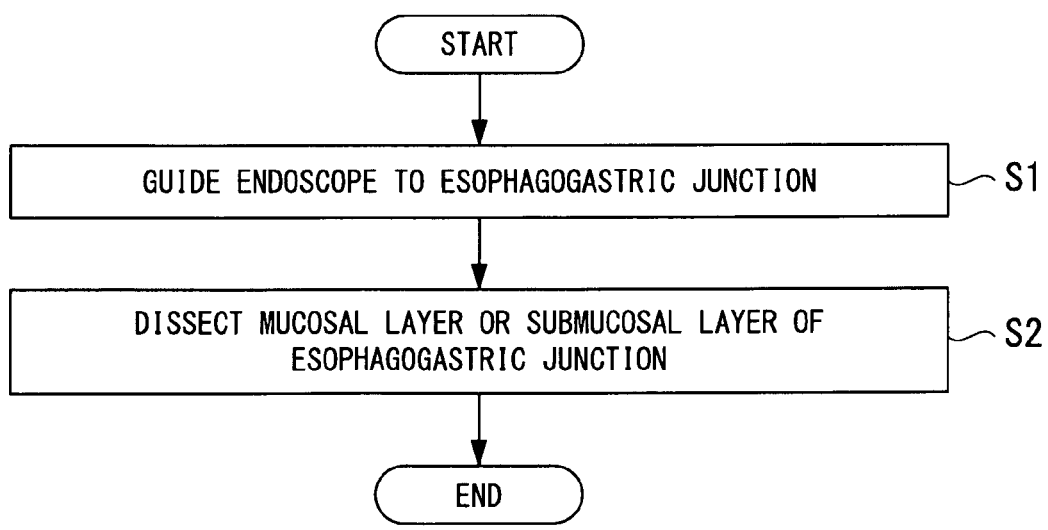
FIG. 3 is a flowchart showing a treatment method in Embodiment 1.

Embodiment 1 of the present invention will be described. FIG. 1 is a diagram schematically showing a dissection area of a mucosal layer or a submucosal layer in Embodiment 1 of the present invention. FIG. 2 is a diagram schematically showing a dissection area of a mucosal layer or a submucosal layer in Embodiment 1. FIG. 3 is a flowchart showing a treatment method in Embodiment 1.

In the present embodiment, as shown in FIG. 1, when gastroesophageal reflux disease occurs due to relaxation of a lower esophageal sphincter while a location of an esophagogastric junction 3 and a location of an esophageal hiatus 9 are substantially the same, cicatricial stenosis is induced near an esophagogastric junction 3 to rebuild a cardiac region 4.

First, an endoscope is guided to the esophagogastric junction 3 (Step S1 in FIG. 3), and a location of a mucosal layer or a submucosal layer (hereinafter referred to as a mucosal layer 5 and the like) to be dissected is determined under the endoscope. Subsequently, the determined dissection target area is dissected using the endoscope (Step S2 in FIG. 3).

The dissection target area in the present embodiment is a part (indicated by area X in FIG. 1) of an entire circumference of the esophagogastric junction 3. An area X in which the mucosal layer 5 and the like are dissected in the present embodiment out of the esophagogastric junction 3 is set to a range of ¼ or more of the entire circumference of the esophagogastric junction 3 and less than the entire circumference thereof. For example, the area X in which the mucosal layer 5 and the like are dissected in the present embodiment out of the esophagogastric junction 3 is an area (indicated by Y in FIG. 2) of ½ or more and ⅔ or less of the entire circumference in the esophagogastric junction 3. In consideration of a junction angle between a stomach 1 and an esophagus 2, when the mucosal layer 5 and the like are dissected in a lesser curvature 1a side of the stomach 1, a clean valve is likely to be formed in the cardiac region 4. Accordingly, it is preferable that the area X in which the mucosal layer 5 and the like are dissected include the lesser curvature 1a side of the stomach 1. Also, in consideration of setting an area for enlarging the cardiac region by Per-Oral Endoscopic Myotomy (POEM) to a greater curvature side and an area for adjusting a shape of the cardiac region 4 by CMR (Cardiac Mucosal Reduction) to a lesser curvature side, when the greater curvature side is allocated for the POEM and the lesser curvature side is allocated for the CMR in the area X in which the mucosal layer 5 and the like are dissected in the present embodiment, it is an excellent setting method in terms of manipulation characteristics.

In the present embodiment, the area X in which the mucosal layer 5 and the like are dissected out of the esophagogastric junction 3 follows in a circumferential direction of the esophagogastric junction 3.

Also, the area X in which the mucosal layer 5 and the like are dissected in the present embodiment out of the esophagogastric junction 3 is set to a continuous range of 30 mm or more and 50 mm or less in a direction from a mouth side to an anus side in an area of the esophagogastric junction 3. The area X in which the mucosal layer 5 and the like are dissected spans a squamocolumnar junction 6.

An area in which the mucosal layer 5 and the like are dissected in the esophagogastric junction 3 is set within an area 30 mm toward the mouth from the squamocolumnar junction 6 and an area 30 mm toward the anus from the squamocolumnar junction 6. When a distance from the mouth side to the anus side is measured in the area in which the mucosal layer 5 and the like are dissected in the esophagogastric junction 3, an area of the mouth side relative to the squamocolumnar junction 6 is wider than an area of the anus side relative to the squamocolumnar junction 6. For example, the area in which the mucosal layer 5 and the like are dissected is set to a continuous area from a location 30 mm from the mouth side from the squamocolumnar junction 6 to a location 20 mm from the anus side from the squamocolumnar junction 6. Also, the area in which the mucosal layer 5 and the like are dissected is set to a continuous area from a location 20 mm from the mouth side from the squamocolumnar junction 6 to a location 10 mm from the anus side from the squamocolumnar junction 6.

Dissection of the mucosal layer 5 and the like in the esophagogastric junction 3 is performed by a known method of endoscopic mucosal resection (EMR) or a known method of endoscopic submucosal dissection (ESD). As the EMR, for example, cap EMR, band ligator EMR, and the like may be used. Tissues dissected through the EMR or the ESD may be disposed in the stomach 1 without being collected when the dissected tissues have no malignant disease.

In addition, in order to accurately dissect tissues in manipulation of the EMR or the ESD, a part to be dissected may be marked before dissection.

When the mucosal layer 5 and the like of the esophagogastric junction 3 are dissected, a basal cell layer of the mucosal layer 5 and the like is defective. In order to repair the basal cell layer, collagenous tissues are accumulated to form a scar. In a process of scar formation, tissues around the scar are pulled in a direction in which the scar is formed. Therefore, an opening 7 of the esophagogastric junction 3 becomes narrower, and the cardiac region 4 having the smaller opening 7 than before the mucosal layer 5 and the like are dissected is rebuilt. In the present embodiment, the narrowed opening 7 formed in the esophagogastric junction 3 is easily closed due to contraction of the lower esophageal sphincter compared to before moderate stenosis is induced.

In addition, when a size of the narrowed opening 7 formed in the esophagogastric junction 3 is not sufficiently narrow to improve gastroesophageal reflux disease and stenosis is insufficient, a mucosal resection range may be further increased in order to further narrow the opening 7. For example, the mucosal layer and the like 5 may be further dissected through the EMR or the ESD to further increase the area dissected using the above manipulation. When the mucosal layer and the like 5 are further dissected, it is possible to increase a degree of constriction in the opening 7 in the present embodiment.

In the related art, as an operation example of the EMR or the ESD in the esophagogastric junction 3, a procedure in which a dissection target region in Barrett's adenocarcinoma is dissected using the EMR or the ESD corresponding to the size of a dissection target region is known. Also, it is known that cicatricial stenosis occurs in some cases after the EMR or the ESD is performed on the esophagus 2 or the stomach 1.

It is known that the cicatricial stenosis in the esophagus 2 or the cardiac region 4 is likely to occur when a circumferential length dissected through the EMR or the ESD out of the entire circumference of the esophagogastric junction 3 is longer. For example, when EMR is performed on the entire circumference or ESD is performed on the entire circumference in the esophagogastric junction 3 and an esophagus stricture or cardia stenosis is caused, treatment for extending a stenosis part using a balloon and the like may be necessary in order to eliminate postprandial dysphagia and the like.

In the present embodiment, since the EMR or the ESD is performed on the area X in a range of ¼ or more of the entire circumference in the esophagogastric junction 3 and less than the entire circumference thereof, the cardiac region 4 is rebuilt by moderate stenosis to an extent that gastric acid reflux from the stomach 1 into the esophagus 2 may not occur, and cardia stenosis causing postprandial dysphagia hardly occurs. In this case, in some areas out of the entire circumference of the esophagogastric junction 3, a non-dissection area having no dissected mucosal layer or submucosal layer is formed. The cardiac region 4 rebuilt by the moderate stenosis is entirely surrounded by the dissection area X and the non-dissection area.

That is, unlike conventional EMR or ESD in which lesions of Barrett's adenocarcinoma and the like are dissected corresponding to the size of the lesions, the present embodiment provides a treatment method in which the optimal dissection area X is set in order to narrow the opening 7 portion of the cardiac region 4 at which stenosis causing postprandial dysphagia does not occur.

(Embodiment 2)

Figure 4:
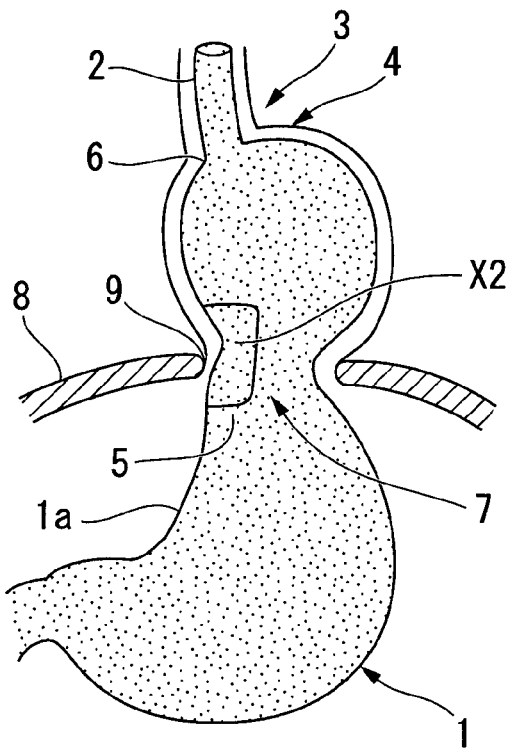
FIG. 4 is a diagram schematically showing a dissection area of a mucosal layer or a submucosal layer in Embodiment 2 of the present invention.
Figure 5:
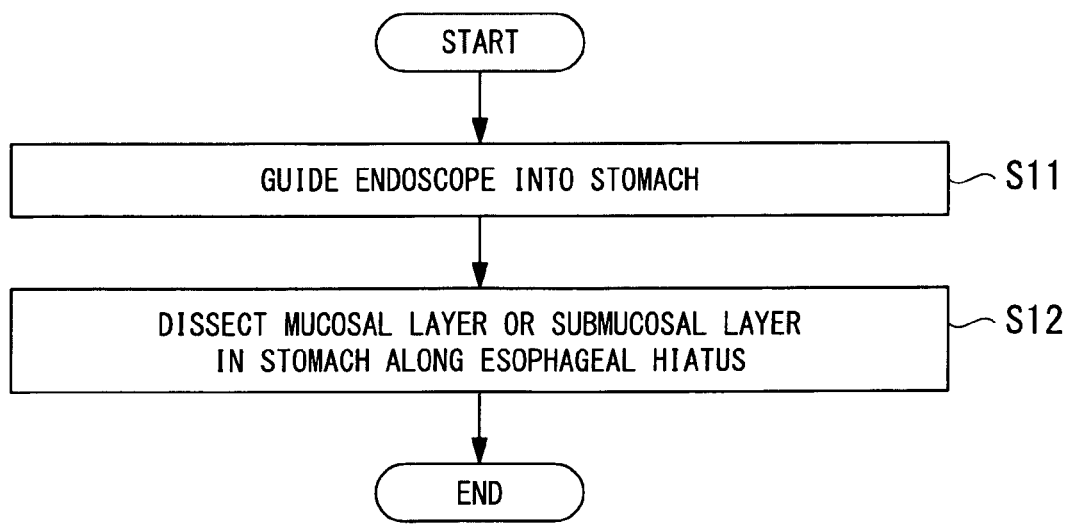
FIG. 5 is a flowchart showing a treatment method of Embodiment 2.

Embodiment 2 of the present invention will be described. FIG. 4 is a diagram schematically showing a dissection area X2 of the mucosal layer and the like 5 in Embodiment 2 of the present invention. FIG. 5 is a flowchart showing a treatment method of Embodiment 2.

In the present embodiment, as shown in FIG. 4, since the lower esophageal sphincter is easily loosened due to a sliding esophageal hiatal hernia in which the esophagogastric junction 3 prolapses to a thoracic cavity side relative to a diaphragm 8, causing gastroesophageal reflux disease, moderate stenosis is induced in the stomach 1 through cicatrization instead of dissection of the mucosal layer and the like 5 in the esophagogastric junction 3.

In the present embodiment, first, the endoscope is guided to an inside of the stomach corresponding to a part clamped by the esophageal hiatus 9 (Step S11 in FIG. 5) out of a part of the stomach 1 that prolapses to a thoracic cavity side relative to the diaphragm 8 due to the sliding esophageal hiatal hernia.

Subsequently, the mucosal layer and the like 5 in the stomach are dissected through the EMR or the ESD (Step S12 in FIG. 5). That is, in the present embodiment, along the esophageal hiatus 9 in a part of the stomach 1 in contact with the esophageal hiatus 9, in a range less than the entire circumference of the stomach 1 including the lesser curvature 1*a* side, the mucosal layer and the like 5 in the stomach 1 are dissected.

Similar to the treatment method described in Embodiment 1, in the present embodiment, the opening 7 narrowed to prevent gastric acid reflux is formed in the stomach 1. That is, in the present embodiment, the opening 7 narrowed by an action of the diaphragm 8 is contracted to prevent gastric acid reflux.

Similar to Embodiment 1, in the present embodiment, it is also possible to treat gastroesophageal reflux disease.
(Embodiment 3)

Figure 6:
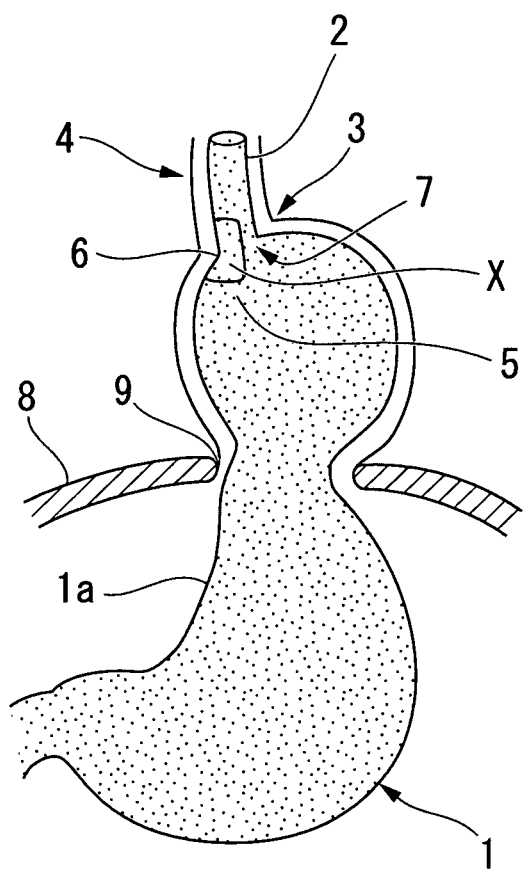
FIG. 6 is a diagram schematically showing a dissection area of a mucosal layer or a submucosal layer in Embodiment 3 of the present invention.

Embodiment 3 of the present invention will be described. FIG. 6 is a diagram schematically showing a dissection area of the mucosal layer and the like 5 in Embodiment 3 of the present invention.

As shown in FIG. 6, in the present embodiment, due to the sliding esophageal hiatal hernia in which the esophagogastric junction 3 prolapses to a thoracic cavity side relative to the diaphragm 8, when the lower esophageal sphincter is easily loosened and causes gastroesophageal reflux disease, cicatricial stenosis is induced near the esophagogastric junction 3 to rebuild the cardiac region 4.

Similar to Embodiment 1, in the present embodiment, the mucosal layer and the like 5 in the esophagogastric junction 3 are dissected through the EMR or ESD.

Similar to Embodiment 1, in the present embodiment, it is also possible to treat gastroesophageal reflux disease.

While preferred embodiments of the present invention have been described above, the present invention is not limited to these embodiments. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of treating gastroesophageal reflux disease, comprising:
   a first step of inserting an endoscope to an esophagastric junction;
   a second step of determining locations of a mucosal layer or a submucosal layer to be dissected on a stomach and the esophogastric junction; and
   a third step of dissecting one of the mucosal layer and the submucosal layer of a lesser curvature side of the stomach and the esophagogastric junction that is next to the lesser curvature side of the stomach while a mucosal layer and a submucosal layer on a greater curvature side of the stomach is not dissected so that partial stenosis occurs due to cicatrization only in an area in which one of the mucosal layer and the submucosal layer of the lesser curvature side of the stomach and the esophagogastric junction that is next to the lesser curvature side of the stomach is dissected.

2. The method of treating gastroesophageal reflux disease according to claim 1,
   wherein one of the mucosal layer and the submucosal layer is dissected in a range of ¼ or more of an entire circumference of the esophagogastric junction and less than the entire circumference thereof, the partial stenosis is induced in the esophagogastric junction, and an opening that is closed by contraction of a lower esophageal sphincter is formed in the esophagogastric junction.

3. The method of treating gastroesophageal reflux disease according to claim 2,
   wherein one of the mucosal layer and the submucosal layer is dissected across a squamocolumnar junction in an area 30 mm toward a mouth from the squamocolumnar junction and in an area 30 mm toward an anus from the squamocolumnar junction out of the esophagogastric junction.

4. The method of treating gastroesophageal reflux disease according to claim 3,
   wherein one of the mucosal layer and the submucosal layer is dissected in an area of 30 mm or more and 50 mm or less from the mouth side to the anus side out of the esophagogastric junction.

5. The method of treating gastroesophageal reflux disease according to claim 4,
   wherein, when a distance from the mouth side to the anus side is measured in the area in which one of the mucosal layer and the submucosal layer is dissected in the esophagogastric junction, an area of the mouth side relative to the squamocolumnar junction is wider than an area of the anus side relative to the squamocolumnar junction.

6. The method of treating gastroesophageal reflux disease according to claim 1,
   wherein, when the esophagogastric junction is located in a thoracic cavity side relative to a diaphragm due to a sliding esophageal hiatal hernia, one of the mucosal layer and the submucosal layer in the stomach is dissected in a range less than an entire circumference of the stomach in a part of the stomach in contact with the esophageal hiatus so that the partial stenosis is induced in the stomach.

7. The method of treating gastroesophageal reflux disease according to claim 1,
   wherein, when the esophagogastric junction is located in a thoracic cavity side relative to a diaphragm due to a sliding esophageal hiatal hernia, the partial stenosis is induced in the esophagogastric junction.

8. The method of treating gastroesophageal reflux disease according to claim 6,
   wherein one of the mucosal layer and the submucosal layer including at least the lesser curvature side of the stomach in at least one of the esophagogastric junction and the stomach is dissected so as to form the partial stenosis.

9. The method of treating gastroesophageal reflux disease according to claim 1,
   wherein one of the mucosal layer and the submucosal layer is dissected across a squamocolumnar junction in an area 30 mm toward a mouth from the squamocolumnar junction and in an area 30 mm toward an anus from the squamocolumnar junction out of the esophagogastric junction.

10. The method of treating gastroesophageal reflux disease according to claim 7,
    wherein one of the mucosal layer and the submucosal layer including at least a lesser curvature side of the stomach in at least one of the esophagogastric junction and the stomach is dissected so as to form the partial stenosis.

* * * * *